(12) United States Patent
Chou et al.

(10) Patent No.: US 7,333,212 B2
(45) Date of Patent: *Feb. 19, 2008

(54) METHOD AND APPARATUS FOR MEASURING THE ABSORPTION COEFFICIENT AND THE REDUCED SCATTERING COEFFICIENT OF A MULTIPLE SCATTERING MEDIUM

(75) Inventors: Chien Chou, 5F, No. 37-3, Chuan-Yuan Rd., Pei-Tou Dist., Taipei City (TW); Yi-Shin Chan, Taipei (TW); Jheng-Syong Wu, Miao-Li Hsien (TW); Li-Ping Yu, Taipei (TW)

(73) Assignee: Chien Chou, Taipei (TW)

( * ) Notice: Subject to any disclaimer, the term of this patent is extended or adjusted under 35 U.S.C. 154(b) by 221 days.

This patent is subject to a terminal disclaimer.

(21) Appl. No.: 11/250,685

(22) Filed: Oct. 14, 2005

(65) Prior Publication Data

US 2006/0033928 A1    Feb. 16, 2006

Related U.S. Application Data

(63) Continuation-in-part of application No. 10/763,655, filed on Jan. 23, 2004, now Pat. No. 7,230,716.

(51) Int. Cl.
*G01B 9/02*    (2006.01)

(52) U.S. Cl. .................................... 356/484; 356/491

(58) Field of Classification Search ................ 356/484, 356/485, 486, 487, 491, 492, 493
See application file for complete search history.

(56) References Cited

U.S. PATENT DOCUMENTS

| | | | | |
|---|---|---|---|---|
| 5,428,447 | A | * | 6/1995 | Toida .......................... 356/601 |
| 6,526,298 | B1 | * | 2/2003 | Khalil et al. ................. 600/310 |
| 7,230,716 | B2 | * | 6/2007 | Chou et al. .................. 356/484 |

* cited by examiner

Primary Examiner—Michael A. Lyons

(57) ABSTRACT

In a method for measuring an absorption coefficient and a reduced scattering coefficient of a multiple scattering medium, a source light beam is outputted, and is transformed into a transformed light beam that includes a mutually parallel circularly polarized photon pair. The transformed light beam is split into a signal beam, which is focused and projected into the multiple scattering medium to produce a diffused polarized photon pair density wave, and a reference beam, which is converted into a reference heterodyne interference signal. The diffused polarized photon pair density wave is converted into a test heterodyne interference signal. Amplitude attenuation and phase delay of the signal beam that has propagated through the multiple scattering medium is obtained based on the reference and test heterodyne interference signals, from which the absorption coefficient and the reduced scattering coefficient of the multiple scattering medium are inferred.

8 Claims, 7 Drawing Sheets

METHOD AND APPARATUS FOR MEASURING THE ABSORPTION COEFFICIENT AND THE REDUCED SCATTERING COEFFICIENT OF A MULTIPLE SCATTERING MEDIUM

CROSS-REFERENCE TO RELATED APPLICATION

This application is a continuation-in-part (CIP) of U.S. patent application Ser. No. 10/763,655 entitled "METHOD FOR MEASURING THE ABSORTPION COEFFICIENT AND THE REDUCED SCATTERING COEFFICIENT OF A MULTIPLE SCATTERING MEDIUM", filed on Jan. 23, 2004 now U.S. Pat No. 7,230,716.

BACKGROUND OF THE INVENTION

1. Field of the Invention

The invention relates to a method for measuring the absorption coefficient and reduced scattering coefficient of a medium, more particularly to a method using circularly polarized photon pairs for measuring the absorption coefficient and reduced scattering coefficient of a multiple-scattering medium.

2. Description of the Related Art

Human tissue is a highly scattering medium, and has the characteristics of having a scattering coefficient much greater than the absorption coefficient thereof. A conventional method of obtaining an image in a scattering medium involves measuring of absorption coefficients so as to obtain an image with contrast. However, when it is desired to obtain the image of an object in a multiple scattering medium, since the light waves are highly scattered, the resultant image is blurred, and the resolution of the image is also reduced considerably. Therefore, if the scattering effect of light in a medium can be reduced, or if only slightly scattered snake photons and ballistic photons are selected, together with enhancement of the sensitivity to absorption coefficients, the resolution of an image in the medium can be enhanced. However, this is not suitable for imaging objects in multiple scattering media.

At present, methods for imaging in a multiple scattering medium mainly include time-domain and frequency-domain imaging techniques. The concept of diffused photon density wave (DPDW) is proposed in the frequency-domain technique. DPDW satisfies the diffusion equation, and can be relied upon to obtain definite amounts of the absorption and scattering coefficients of a test object, such as a tumor, thereby permitting recovery of an image of the test object in the scattering medium. The frequency-domain technique is currently more suitable for imaging in a multiple scattering medium, but has the drawback that the spatial resolution is not high. Thus, how to enhance imaging resolution in applications that involve a multiple scattering medium is currently an important topic in the industry.

In co-pending U.S. patent application Ser. No. 10/763,655 entitled "METHOD FOR MEASURING THE ABSORTPION COEFFICIENT AND THE REDUCED SCATTERING COEFFICIENT OF A MULTIPLE SCATTERING MEDIUM", filed on Jan. 23, 2004, there is disclosed a method for measuring absorption and reduced scattering coefficients of a multiple scattering medium, in which a coherent light beam is outputted. The coherent light beam includes linearly polarized P and S wave components having mutually orthogonal polarizations and frequencies $\omega_P$ and $\omega_S$, respectively. Then, the coherent light beam is split into a signal beam and a reference beam, which include the P and S wave components. The signal beam is subsequently projected into the medium. Optical interference signals of the reference beam and the signal beam penetrating the medium are respectively detected and converted into heterodyne interference electrical signals. Thereafter, the two heterodyne interference electrical signals are compared to obtain is amplitude attenuation and phase delay of the signal beam penetrating the medium, from which the absorption and reduced scattering coefficients of the medium at a position where the signal beam penetrated the medium are inferred.

SUMMARY OF THE INVENTION

The main object of the present invention is to provide a method for measuring the absorption coefficient and reduced scattering coefficient of a multiple scattering medium using a circularly polarized photon pair.

Another object of the present invention is to provide a method using a circularly polarized photon pair for constructing an image of an object in a multiple scattering medium.

Yet another object of the present invention is to provide a method for measuring Oxygenation saturation ($S_aO_2$) and changes thereof in a multiple scattering medium using two circularly polarized photon pairs, each having a distinct center frequency.

A further object of the present invention is to provide a spectrometer apparatus for measuring the $S_aO_2$ and changes thereof in a multiple scattering medium using a plurality of circularly polarized photon pairs, each having a distinct center frequency.

According to a first aspect of the present invention, there is provided a method for measuring an absorption coefficient and a reduced scattering coefficient of a multiple scattering medium, comprising the steps of: outputting a source light beam using a two-frequency polarized laser, the source light beam including a mutually correlated and mutually orthogonal polarized photon pair; transforming the source light beam into a transformed light beam that includes a mutually parallel circularly polarized photon pair, the mutually parallel circularly polarized photon pair being one of a pair of R waves and a pair of L waves; splitting the transformed light beam into a signal beam and a reference beam; detecting and converting the reference beam into a reference heterodyne interference signal; focusing the signal beam and projecting the focused signal beam into the multiple scattering medium via an optical signal fiber to produce a diffused polarized photon pair density wave; detecting the diffused polarized photon pair density wave via an optical detection fiber that is spaced apart from the optical signal fiber; converting the diffused polarized photon pair density wave into a test heterodyne interference signal; obtaining amplitude attenuation and phase delay of the signal beam that has propagated through the multiple scattering medium based on the reference and test heterodyne interference signals; and inferring the absorption coefficient and the reduced scattering coefficient of the multiple scattering medium with reference to the amplitude attenuation and the phase delay thus obtained.

According to a second aspect of the present invention, there is provided a method for measuring an absorption coefficient and a reduced scattering coefficient of a multiple scattering medium, comprising the steps of: outputting a source light beam using a two-frequency circularly polarized laser, the source light beam including a mutually correlated and mutually orthogonal circularly polarized photon pair, the mutually correlated and mutually orthogonal circularly polarized photon pair including an R wave and an L wave; splitting the source light beam into a signal beam and a reference beam; converting the reference beam into a mutually parallel polarized photon pair via a polarizer; detecting and further converting the reference beam with the mutually parallel polarized photon pair into a reference heterodyne interference signal; focusing the signal beam and projecting the focused signal beam into the multiple scattering medium via an optical signal fiber to produce a diffused polarized photon pair density wave; detecting the diffused polarized photon pair density wave via an optical detection fiber that is spaced apart from the optical signal fiber; converting the detected diffused polarized photon pair density wave into a mutually parallel polarized photon pair; further converting the mutually parallel polarized photon pair converted from the detected diffused polarized photon pair density wave into a test heterodyne interference signal; obtaining amplitude attenuation and phase delay of the signal beam that has propagated through the multiple scattering medium based on the reference and test heterodyne interference signals; and inferring the absorption coefficient and the reduced scattering coefficient of the multiple scattering medium with reference to the amplitude attenuation and the phase delay thus obtained.

According to a third aspect of the present invention, there is provided a method for measuring an absorption coefficient and a reduced scattering coefficient of a multiple scattering medium, comprising the steps of: outputting source light beams from a set of two-frequency circularly polarized lasers, the source light beams having distinct center frequencies, each of the source light beams including a mutually correlated and mutually orthogonal circularly polarized photon pair, the mutually correlated and mutually orthogonal circularly polarized photon pair of each of the source light beams including an R wave and an L wave; transforming each of the source light beams into a corresponding transformed light beam that includes a mutually parallel circularly polarized photon pair, the mutually parallel circularly polarized photon pair of each of the transformed light beams being one of a pair of R waves and a pair of L waves; splitting the transformed light beams into a signal beam and a reference beam; detecting and converting the reference beam into a set of filtered reference heterodyne interference signals; focusing the signal beam and projecting the focused signal beam into the multiple scattering medium via an optical signal fiber to produce a diffused polarized photon pair density wave; detecting the diffused polarized photon pair density wave via an optical detection fiber that is spaced apart from the optical signal fiber; converting the diffused polarized photon pair density wave into a set of filtered test heterodyne interference signals; obtaining amplitude attenuation and phase delay of the signal beam that has propagated through the multiple scattering medium based on the filtered reference and test heterodyne interference signals; and inferring the absorption coefficient and the reduced scattering coefficient of the multiple scattering medium with reference to the amplitude attenuation and the phase delay thus obtained.

According to a fourth aspect of the present invention, there is provided a spectrometer apparatus adapted for measuring an absorption coefficient and a reduced scattering coefficient of a multiple scattering medium, the spectrometer apparatus comprising: a set of two-frequency circularly polarized lasers for outputting a set of source light beams, the source light beams having distinct center frequencies, each of the source light beams including a mutually correlated and mutually orthogonal circularly polarized photon pair, the mutually correlated and mutually orthogonal circularly polarized photon pair of each of the source light beams including an R wave and an L wave; a set of beam-transforming units, each including a first $\lambda/4$ wave plate, a polarizer, and a second $\lambda/4$ wave plate arranged in sequence at an output side of a respective one of the lasers, each of the beam-transforming units transforming a respective one of the source light beams into a transformed light beam that includes a mutually parallel circularly polarized photon pair, the mutually parallel circularly polarized photon pair of each of the transformed light beams being one of a pair of R waves and a pair of L waves; a beam splitter for splitting the transformed light beams from the beam-transforming units into a signal beam and a reference beam; a set of first photo detectors for detecting the reference beam from the beam splitter, and a set of reference band-pass filters coupled respectively to the first photo detectors, the reference band-pass filters having distinct pass-band frequency ranges, and converting the reference beam detected by the first photo detectors into a set of filtered reference heterodyne interference signals; an object lens for focusing the signal beam from the beam splitter; an optical signal fiber adapted for projecting the focused signal beam from the object lens into the multiple scattering medium to produce a diffused polarized photon pair density wave; an optical detection fiber spaced apart from the optical signal fiber and adapted for detecting the diffused polarized photon pair density wave; a set of second photo detectors for receiving the diffused polarized photon pair density wave detected by the optical detection fiber, and a set of test band-pass filters coupled respectively to the second photo detectors, the test band-pass filters having distinct pass-band frequency ranges, and converting the diffused polarized photon pair density wave processed by the second photo detectors into a set of filtered test heterodyne interference signals; a set of signal processors, each of which is coupled to a respective one of the reference band-pass filters and a respective one of the test band-pass filters, each of the signal processors obtaining amplitude attenuation and phase delay of the signal beam that has propagated through the multiple scattering medium based on the filtered reference and test heterodyne interference signals received thereby, and inferring the absorption coefficient and the reduced scattering coefficient of the multiple scattering medium with reference to the amplitude attenuation and the phase delay obtained thereby.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1A:
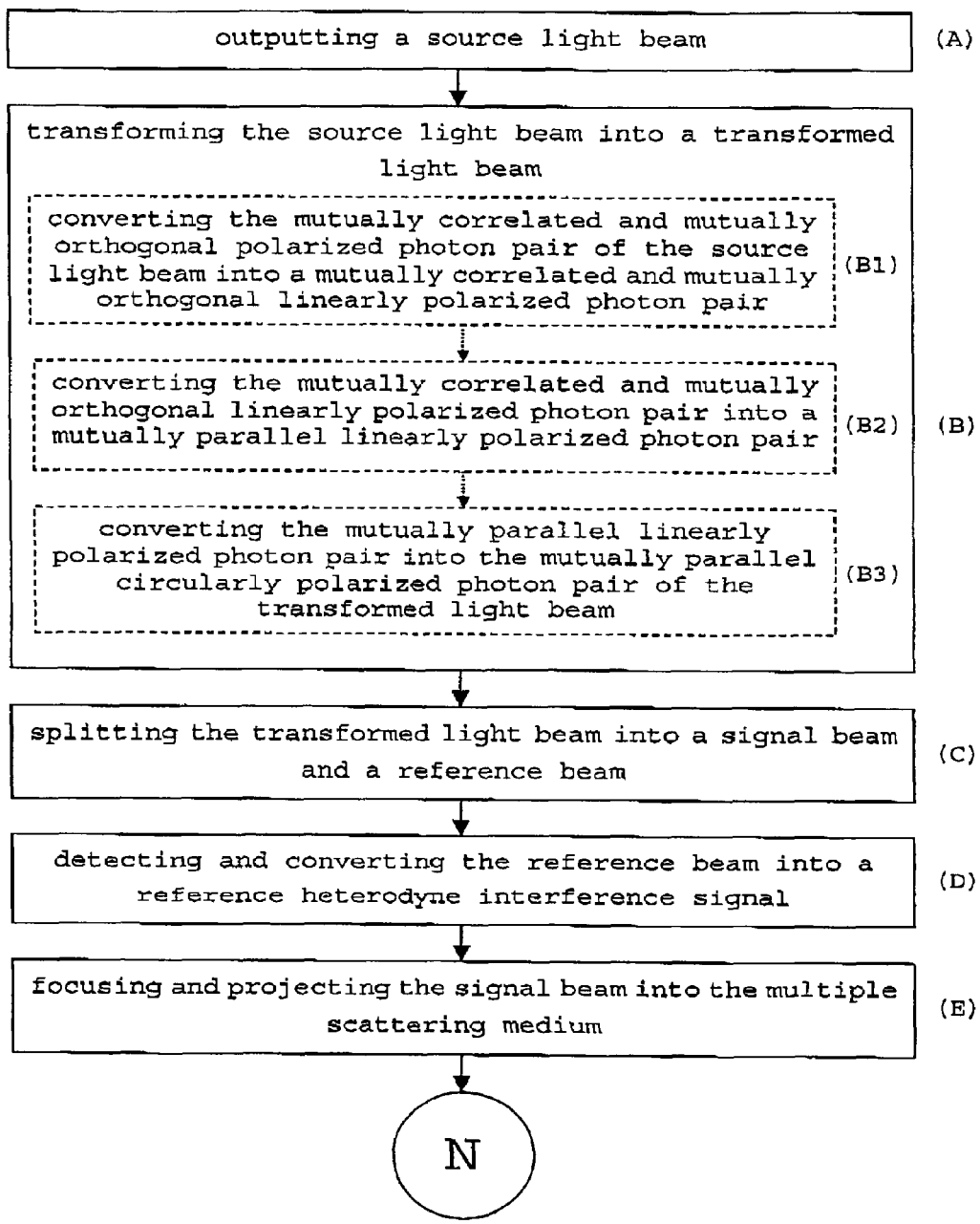
FIGS. 1a and 1b are flow charts of a method for measuring the absorption coefficient and the reduced scattering coefficient of a multiple scattering medium according to the first preferred embodiment of the present invention.

Before the present invention is described in greater detail, it should be noted herein that like elements are denoted by the same reference numerals throughout the disclosure.

Figure 1B:
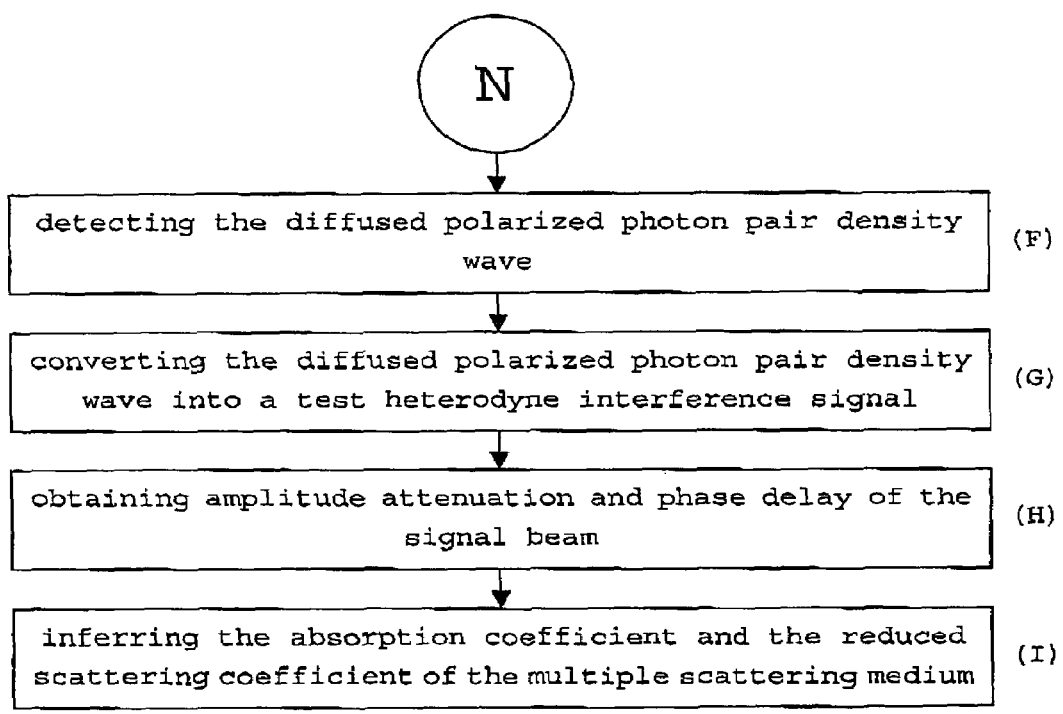

As shown in FIGS. 1a and 1b, a method for measuring an absorption coefficient $\mu_a$ and a reduced scattering coefficient $\mu_s'$ of a multiple scattering medium according to the first preferred embodiment of the present invention comprises the following steps:

(A) Outputting a source light beam using a two-frequency circularly polarized laser, such as a Zeeman He—Ne laser or other two-frequency semiconductor lasers. The source light beam in this embodiment includes a mutually correlated and mutually orthogonal circularly polarized photon pair (CPPP) that has a center wavelength $\lambda_1$ and that includes an R wave and an L wave having frequencies $\omega_R$ and $\omega_L$, respectively.

(B) Transforming the source light beam into a transformed light beam that includes a mutually parallel CPPP, which is one of a pair of R waves and a pair of L waves. In this embodiment, the source light beam is transformed into the transformed light beam by a series of sub-steps.

(B1) The mutually correlated and mutually orthogonal CPPP of the source light beam is converted into a mutually correlated and mutually orthogonal linearly polarized photon pair, which includes a P wave and an S wave having frequencies $\omega_R$ and $\omega_L$, respectively, using a first quarter-wave plate ($\lambda/4$ wave plate).

(B2) The mutually correlated and mutually orthogonal linearly polarized photon pair is converted into a mutually parallel linearly polarized photon pair via a polarizer or an analyzer.

(B3) The mutually parallel linearly polarized photon pair is converted into the mutually parallel CPPP of the transformed light beam through a second $\lambda/4$ wave plate.

It should be noted herein that the purpose of the aforesaid steps (A) and (B1) is to produce a mutually correlated and mutually orthogonal linearly polarized photon pair. This can also be achieved by outputting the source light beam using a two-frequency linearly polarized laser, where the source light beam includes a mutually correlated and mutually orthogonal linearly polarized photon pair, in other embodiments of the present invention.

(C) Splitting the transformed light beam into a signal beam and a reference beam using a beam splitter.

(D) Detecting and converting the reference beam into a reference heterodyne interference signal using a photo detector. The reference heterodyne interference signal is subsequently fed into an electrical signal processor as a reference for phase measurements of the signal beam. The intensity of the reference heterodyne interference signal thus generated can be expressed as follows:

$$I_r(\Delta\omega t) = DC + \Gamma \cos(\Delta\omega t) \quad (1)$$

(E) Focusing the signal beam using a microscopic object lens, and projecting the focused signal beam into the multiple scattering medium via an optical signal fiber to produce a diffused polarized photon pair density wave (DPPDW), which satisfies the diffusion equation. When the CPPP of the signal beam is projected into the multiple scattering medium, the spatial coherence and degree of polarization (DOP) of most of the CPPP are destroyed due to a series of collision events. Those of the CPPP that undergo less collision events remain correlated and contribute to the generation of DPPDW, since relatively more polarization characteristics and directionality are preserved.

(F) Detecting the DPPDW via an optical detection fiber that is spaced apart at a separation distance r from the signal optical fiber.

(G) Converting the detected DPPPW into a test heterodyne interference signal using a photo multiplier tube. The intensity of the test heterodyne interference signal can be expressed as follows:

$$I(\Delta\omega t) = DC + \gamma \cos(\Delta\omega t + \Delta\Phi) \quad (2)$$

The test heterodyne interference signal is outputted through a signal amplifier, and a band-pass filter (BPF) with a center frequency $\Delta\omega = \omega_R - \omega_L$ to the electrical signal processor.

(H) obtaining amplitude attenuation and phase delay of the signal beam that has propagated through the multiple scattering medium based on the reference and test heterodyne interference signals.

Since the DPPDW in a homogenous scattering medium is a spherical wave, the intensity thereof is related to the rate of energy fluence $\phi_0^2$ of the DPPDW, the real part $k_{2r}$ of the wave number $k_2$, and the separation distance r, and satisfies $$I(\Delta\omega t) = \varphi_0^2 \frac{e^{-k_{2r} r}}{r} \text{Re}\{e^{i(\Delta\omega t + \Delta\phi)}\} \quad (3)$$

from which, the amplitude attenuation of the signal beam in the multiple scattering medium at different separation distances $r_0$ and r can be obtained and is expressed as $$\ln\left(\frac{I}{I_o}\right) = \left[\ln\left(\frac{r_o}{r}\right) - k_{2r}\Delta r\right] \quad (4)$$

in which $k_{2r}$ corresponds to the absorption characteristics of the signal beam in the multiple scattering medium, and is related to the absorption coefficient $\mu_a$ and the reduced scattering coefficient $\mu_s'$.

$$k_{2r} = [3\mu_a(\mu_s' + \mu_a)]^{1/2} \quad (5)$$

Phase measurements can also be obtained by the electrical signal processor, where phase delay is related to the imaginary part $k_{2i}$ of the wave number $k_2$ and the separation distance r, and satisfies $$\Delta \phi = \frac{n\Delta \omega}{c} \left( \frac{3\mu'_s}{4\mu_a} \right)^{\frac{1}{2}} \cdot r = k_{2i} r \qquad (6)$$

in which $k_{2i}$ corresponds to the scattering characteristics of the signal beam in the scattering medium, whose relation with the refractive index, the absorption coefficient $\mu_a$, and the reduced scattering coefficient $\mu_g'$ are as expressed in Equation (7).

$$k_{2i} = \frac{n\Delta \omega}{c} \left( \frac{3\mu'_s}{4\mu_a} \right)^{\frac{1}{2}} \qquad (7)$$

(I) Inferring the absorption coefficient $\mu_a$ and the reduced scattering coefficient $\mu_g'$ of the multiple scattering medium with reference to the amplitude attenuation and the phase delay thus obtained. The absorption coefficient $\mu_a$ and the reduced scattering coefficient $\mu_g'$ can be obtained from Equation (5) and Equation (7), and are expressed respectively in the following equations.

$$\mu_a = \frac{n\Delta \omega}{2c} \left( \frac{k_{2r}}{k_{2i}} \right) \qquad (8)$$

$$\mu'_s = \frac{2c k_{2r} k_{2i}}{3n(\Delta \omega)} \qquad (9)$$

Therefore, the three-dimensional (3-D) spatial distributions of the absorption coefficient $\mu_a$ and reduced scattering coefficient $\mu_g'$ are obtained by finding the solution to the diffusion equation so as to obtain optical characteristics of an image in the multiple scattering medium, thereby achieving image recovery in the multiple scattering medium in order to solve the problem of poor spatial imaging resolution of the prior art.

Furthermore, as oxyhemoglobin ($HbO_2$) and Deoxyhemoglobin (Hb) have different absorption coefficients $\mu_a$ with respect to different wavelengths, such as that of red light and blue light, by using a mutually correlated and mutually orthogonal CPPP emitted by a two-frequency circularly polarized laser source and having a center wavelength $\lambda_2$, the corresponding absorption coefficients $\mu_a$ can be obtained by the aforesaid process. The concentration of $HbO_2$ and Hb can then be calculated, and the oxygenation saturation ($S_aO_2$) can be measured to obtain images of $S_aO_2$ distribution.

Figure 2:
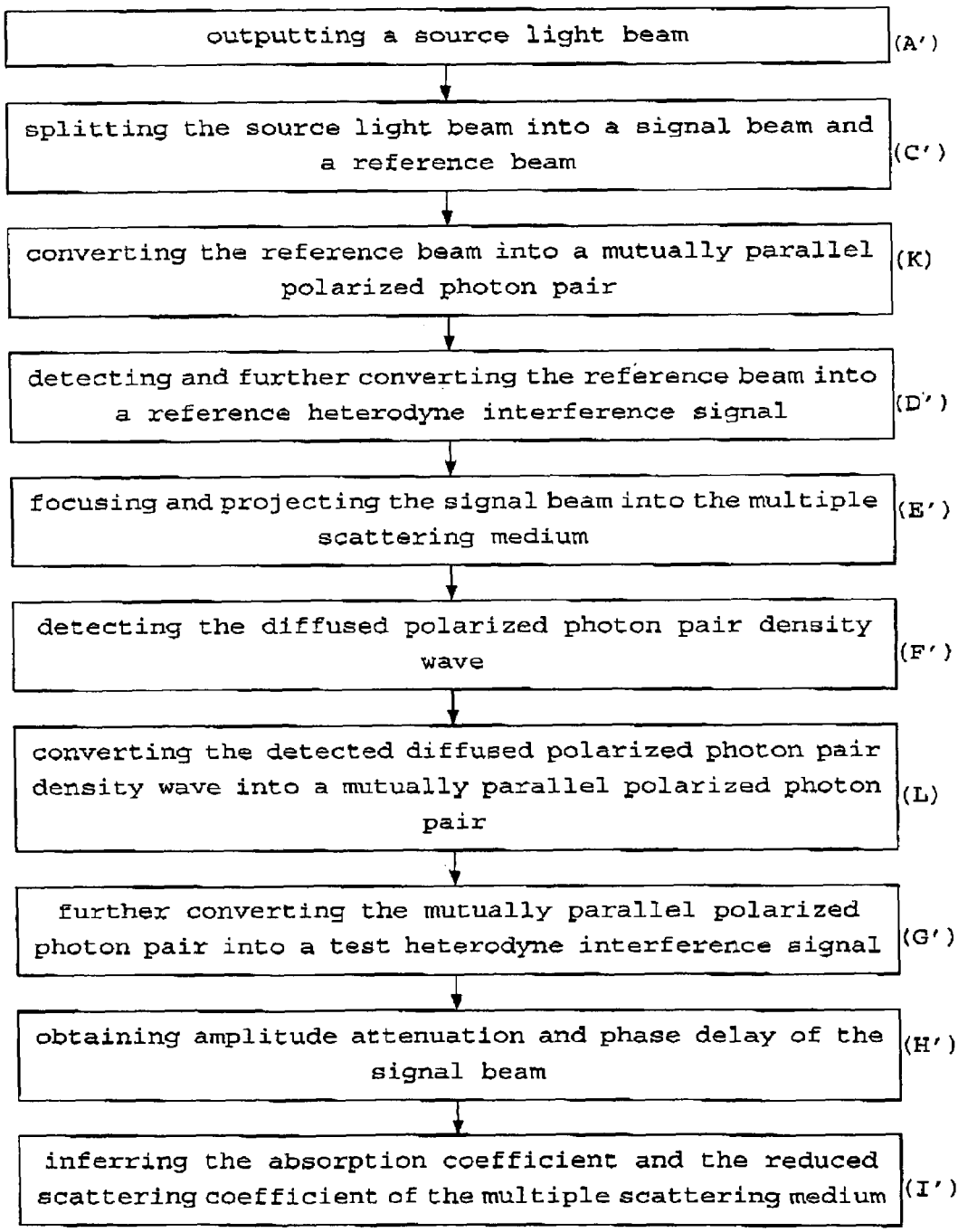
FIG. 2 is a flow chart of a method for measuring the absorption coefficient and the reduced scattering coefficient of a multiple scattering medium according to the second preferred embodiment of the present invention.

As shown in FIG. 2, a method for measuring the absorption coefficient $\mu_a$ and the reduced scattering coefficient $\mu_g'$ of the multiple scattering medium according to the second preferred embodiment of the present invention differs from that in the first preferred embodiment in that the source light beam that includes a mutually correlated and mutually orthogonal circularly polarized photon pair is not transformed into a transformed light beam that includes a mutually parallel circularly polarized photon pair as in step (B) in the first preferred embodiment. Instead, the source light beam is split directly in step (C') into a signal beam and a reference beam, each including a mutually orthogonal polarized photon pair, instead of a mutually parallel polarized photon pair as in the first preferred embodiment. The reference beam is converted into a mutually parallel polarized photon pair in step (K), which is detected and further converted into a reference heterodyne interference signal instep (D') The signal beam is focused and projected into the multiple scattering medium to produce a DPPDW in step (E'). The DPPDW is detected in step (F'), and is converted into a mutually parallel polarized photon pair in step (L). The mutually parallel polarized photon pair is further converted into a test heterodyne interference signal in step (G'). The absorption coefficient $\mu_a$ and the reduced scattering coefficient $\mu_g'$ of the multiple scattering medium are then obtained in the same way as explained in the first preferred embodiment, and will not be repeated herein for the sake of brevity.

Figure 3:
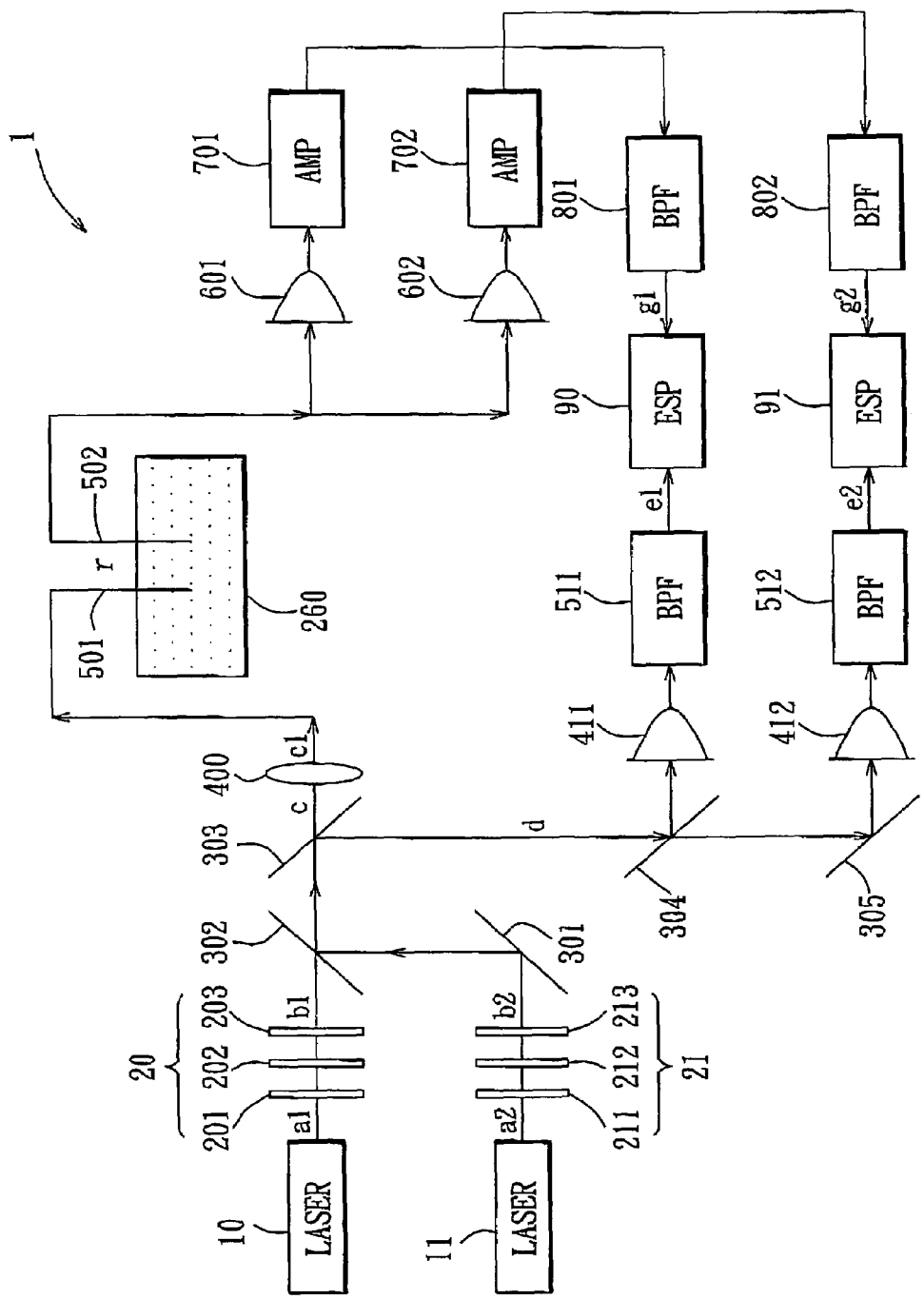
FIG. 3 is a block diagram of a spectrometer apparatus adapted for measuring an absorption coefficient and a reduced scattering coefficient of a multiple scattering medium according to the third preferred embodiment of the present invention.

As shown in FIG. 3, a spectrometer apparatus 1 adapted for measuring an absorption coefficient $\mu_a$ and a reduced scattering coefficient $\mu_g'$ of a multiple scattering medium 260 according to the third preferred embodiment of the present invention includes first and second two-frequency circularly polarized lasers 10, 11 for outputting first and second source light beams (a1), (a2), respectively. The first and second source light beams (a1), (a2) have distinct center frequencies with corresponding first and second center wavelengths $\lambda_1$, $\lambda_2$. Each of the first and second source light beams (a1), (a2) includes a mutually correlated and mutually orthogonal circularly polarized photon pair (CPPP), each of which includes an R wave and an L wave having frequencies $\omega_R$ and $\omega_L$, respectively. In this embodiment, the first and second two-frequency circularly polarized lasers 10, 11 are both two-frequency semiconductor lasers, and $\lambda_1=780$ nm, $\lambda_2=850$ nm. In addition, the mutually orthogonal CPPP of the first and second source light beams (a1), (a2) have different beat frequencies, i.e., the differences between $\omega_R$ and $\omega_L$ are dissimilar, The multiple scattering medium 260 is hemoglobin in blood in this embodiment.

The spectrometer apparatus 1 further includes first and second beam-transforming units 20, 21, each of which includes a first $\lambda/4$ wave plate 201, 211, a polarizer 202, 212, and a second $\lambda/4$ wave plate 203, 213 arranged in sequence at an output side of a respective one of the first and second two-frequency circularly polarized lasers 10, 11. The first and second beam-transforming units 20, 21 transform the first and second source light beams (a1), (a2) respectively into first and second transformed light beams (b1), (b2), each of which includes a mutually parallel CPPP, in a manner explained hereinbelow. Each of the mutually orthogonal CPPP from the respective one of the first and second two-frequency circularly polarized lasers 10, 11 is passed through the first $\lambda/4$ wave plate 201, 211 of the respective one of the first and second beam-transforming unit 20, 21 for conversion into a mutually correlated and mutually orthogonal linearly polarized photon pair that includes a P wave and an S wave, the temporal frequencies of which being $\omega_R$ and $\omega_L$, respectively. Each of the mutually correlated and mutually orthogonal linearly polarized photon pairs is then converted into a mutually parallel linearly polarized photon pair via the respective one of the polarizers 202, 212. Each of the mutually parallel linearly polarized photon pairs is subsequently converted into a mutually parallel CPPP after passing through the respective one of the second $\lambda/4$ wave plates 203, 213, wherein the mutually parallel CPPP of each of the first and second transformed light beams (b1), (b2) is one of a pair of R waves and a pair of L waves.

The spectrometer apparatus 1 further includes first and second beam splitters 302, 303, and a reflective mirror 301 arranged after the second $\lambda/4$ waveplate 213 to reflect the second transformed light beam (b2) toward the first beam splitter 302 for combining with the first transformed light beam (b1). The second beam splitter 303 is for splitting the first and second transformed light beams (b1), (b2) from the first and second beam-transforming units 20, 21 into a signal beam (c) and a reference beam (d).

The spectrometer apparatus 1 further includes first and second photo detectors 411, 412 for detecting the reference beam (d) from the second beam splitter 303 via a third beam splitter 304 and a second reflector 305, respectively, and first and second reference band-pass filters (BPFs) 511, 512 coupled respectively to the first and second photo detectors 411, 412. The first and second reference band-pass filters 511, 512 have distinct pass-band frequency ranges corresponding respectively to the first and second center wavelengths $\lambda_1, \lambda_2$, to convert the reference beam (d) detected by the photo detectors 411, 412 into first and second filtered reference heterodyne interference signals (e1), (e2).

The spectrometer apparatus 1 further includes a microscopic object lens 400 for focusing the signal beam (c) from the second beam splitter 303, an optical signal fiber 501 adapted for projecting the focused signal beam (c1) from the object lens 400 into the multiple scattering medium 260 to produce a diffused polarized photon pair density wave (DPPDW), and an optical detection fiber 502 spaced apart at a separation distance r from the optical signal fiber 501 and adapted for detecting the DPPDW.

The spectrometer apparatus 1 further includes first and second photo-multiplier tubes 601, 602 and first and second signal amplifiers (AMPs) 701, 702 for receiving and amplifying the DPPDW detected by the optical detection fiber 502, and first and second signal band-pass filters (BPFs) 801, 802 coupled respectively to the first and second signal amplifiers 701, 702. The first and second signal band-pass filters 801, 802 have distinct pass-band frequency ranges corresponding respectively to the first and second center wavelengths $\lambda_1, \lambda_2$, to convert the DPPDW processed by the first and second photo-multiplier tubes 601, 602 and the first and second signal amplifiers (AMPs) 701, 702 into first and second filtered test heterodyne interference signals (g1), (g2). Since the aforesaid DPPDW consists of waves having distinct center wavelengths, i.e., the first and second center wavelengths $\lambda_1, \lambda_2$, by using band-pass filters with different pass-band frequency ranges, or by using two different optical filters, corresponding signals of interest can be extracted.

The spectrometer apparatus 1 further includes first and second electrical signal processors (ESPs) 90, 91, each of which is coupled to a respective one of the first and second reference band-pass filters 511, 512 and a respective one of the first and second electrical signal band-pass filters (ESPs) 801, 802. Each of the first and second signal processors 90, 91 obtains amplitude attenuation and phase delay of the signal beam (c) that has propagated through the multiple scattering medium 260 based on the respective pair of the filtered reference and test heterodyne interference signals (e1), (e2), (g1), (g2) received thereby. The first and second signal processors 90, 91 then infer the absorption coefficients $\mu_a$ and the reduced scattering coefficients $\mu_s'$ of the multiple scattering medium 260 respectively at the first and second center wavelengths $\lambda_1, \lambda_2$ with reference to the amplitude attenuation and the phase delay obtained thereby. In this embodiment, the first and second electrical signal processors (ESPs) 90, 91 are phase-locking amplifiers.

Since the absorption coefficients $\mu_a$ of hemoglobin in the blood in an oxygenated state (HbO$_2$) and in a deoxygenated state (Hb) are obviously different with respect to different wavelengths $\lambda_1$ and $\lambda_2$, changes in the hemoglobin saturation (SaO$_2$) can be obtained in real time from Equations (10) to (13).

$$\Delta\mu_a(\lambda_1) = \varepsilon_{Hb}^{\lambda_1}\Delta Hb + \varepsilon_{HbO_2}^{\lambda_1}\Delta HbO_2 \tag{10}$$

$$\Delta\mu_a(\lambda_2) = \varepsilon_{Hb}^{\lambda_2}\Delta Hb + \varepsilon_{HbO_2}^{\lambda_2}\Delta HbO_2 \tag{11}$$

$$\Delta Hb = \frac{\varepsilon_{HbO_2}^{\lambda_2}\Delta\mu_{2a}^{\lambda_1} - \varepsilon_{HbO_2}^{\lambda_1}\Delta\mu_{2a}^{\lambda_2}}{(\varepsilon_{Hb}^{\lambda_1}\varepsilon_{HbO_2}^{\lambda_2} - \varepsilon_{Hb}^{\lambda_2}\varepsilon_{HbO_2}^{\lambda_1})} \tag{12}$$

$$\Delta HbO_2 = \frac{\varepsilon_{Hb}^{\lambda_2}\Delta\mu_{2a}^{\lambda_1} - \varepsilon_{Hb}^{\lambda_1}\Delta\mu_{2a}^{\lambda_2}}{(\varepsilon_{HbO_2}^{\lambda_1}\varepsilon_{Hb}^{\lambda_2} - \varepsilon_{HbO_2}^{\lambda_2}\varepsilon_{Hb}^{\lambda_1})} \tag{13}$$

As relevant theories can be found in published literature, such as H. Liu et al., "Noninvasive investigation of blood oxygenation dynamics of tumors by near infrared spectroscopy," *Applied Optics* 39, 5231-5243(2000), further details are omitted herein.

Moreover, it should be noted herein that the number of laser sources to be included is not limited to two, and application is not limited to hemoglobin measurements in other embodiments of the present invention. If measurements of $\mu_a$ and $\mu_s'$ in a scattering medium are desired, only one two-frequency laser may suffice.

Figure 4A:
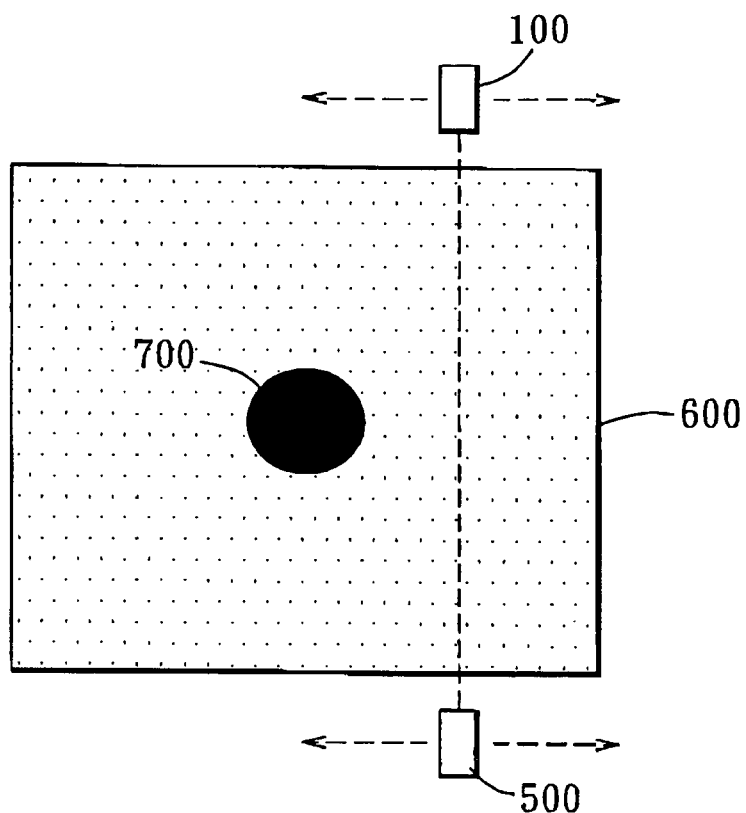
FIG. 4a is a schematic view of a penetrative spatial scanning employed in the fourth preferred embodiment of the present invention.
Figure 4B:
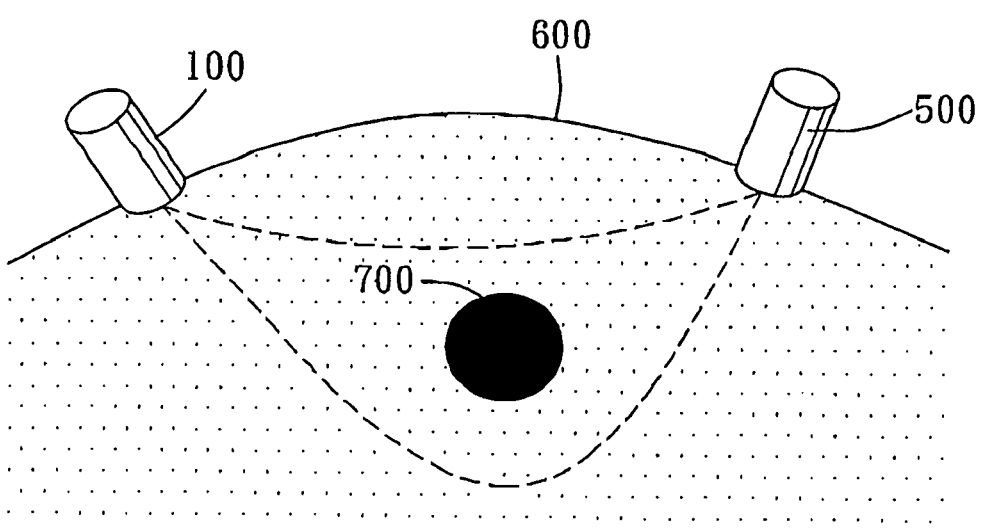
FIG. 4b is a schematic view of a reflective spatial scanning employed in the fourth preferred embodiment.

As shown in FIG. 4a and FIG. 4b, a two-frequency laser 100 and a detector 500, which includes an optical detection fiber, are displaced together relative to a multiple scattering medium 600, such as human tissue, skull, etc., to perform two-dimensional (2-D) penetrative spatial scanning and three-dimensional (3-D) reflective spatial scanning in the fourth preferred embodiment of the present invention. The spatial distributions of $\mu_s'$ and $\mu_a$ are obtained from the phase and amplitude data of DPPDW. The image of an object 700 in the multiple scattering medium 600 is then recovered using the diffusion equation. The number of two-frequency lasers 100 and detectors 500 to be included depends on imaging requirements of a particular application.

Figure 5:
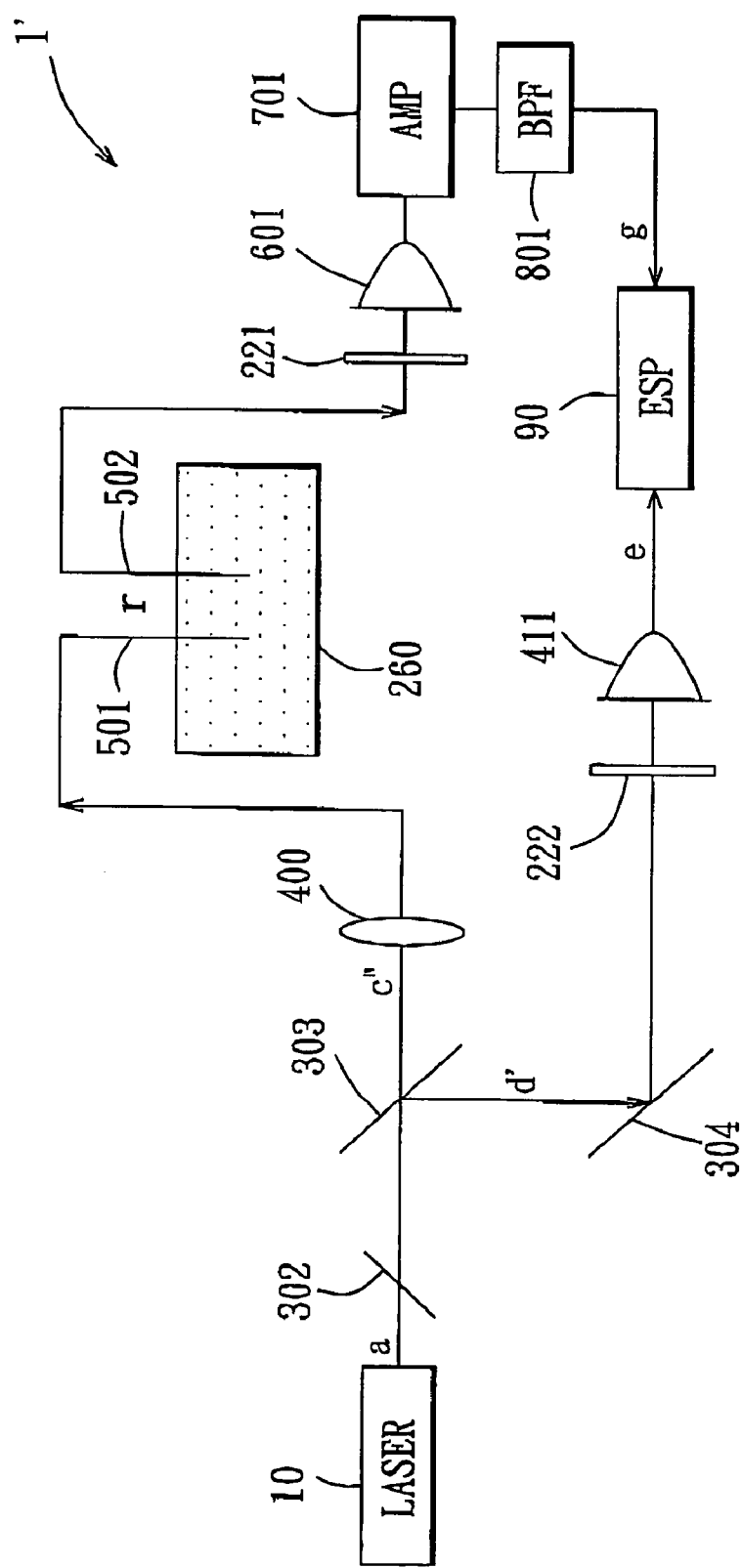
FIG. 5 is a block diagram of a spectrometer apparatus for implementing the method according to the second preferred embodiment of the present invention.

Shown in FIG. 5 is a spectrometer apparatus 1' implementing the method according to the second preferred embodiment of the present invention. The spectrometer apparatus 1' is adapted for measuring the absorption coefficient $\mu_a$ and the reduced scattering coefficient $\mu_s'$ of the multiple scattering medium 260, and differs from the spectrometer apparatus 1 of the third preferred embodiment in that there is one, instead of two, two-frequency circularly polarized laser 10, and accordingly one photo detector 411, one photo-multiplier tube 601, one signal amplifier (AMP) 701, one band-pass filter (BPF) 801, and one electrical signal processor (ESP) 90. The two-frequency circularly polarized laser 10 emits a source light beam (a) that includes a mutually correlated and mutually orthogonal CPPP. In addition, the spectrometer apparatus 1' does not include the beam-transforming unit 20 of the third preferred embodiment. Instead, first polarizer 221 is disposed after the detector optical fiber 502 and before the photo-multiplier tube 601.

In this embodiment, the source light beam (a) is split into a signal beam (c") and a reference beam (d') directly after being outputted from the two-frequency circularly polarized laser 10 through the beam splitter 303, and the signal beam (c") is focused via the microscopic object lens 400 and projected into the multiple scattering medium 260 via the optical signal fiber 501. The DPPDW is detected via the optical detection fiber 502, and subsequently passes through the first polarizer 221 for conversion into a mutually parallel linearly polarized photon pair, which is further converted into a filtered test heterodyne interference signal (g) through the photo-multiplier tube 601, the signal amplifier (AMP) 701 and the band-pass filter (BPF) 801, that is outputted to the electrical signal processor 90. On the other hand, the reference beam (d') is converted into a mutually parallel linearly polarized photon pair via the second polarizer 222, and subsequently outputted to the photo detector 411 for conversion into a reference heterodyne interference signal (e), which is sent to the electrical signal processor 90 to obtain the absorption coefficient $\mu_a$ and reduced scattering coefficient $\mu_g'$ in the manner explained hereinabove in connection with the previous embodiments.

Figure 6:
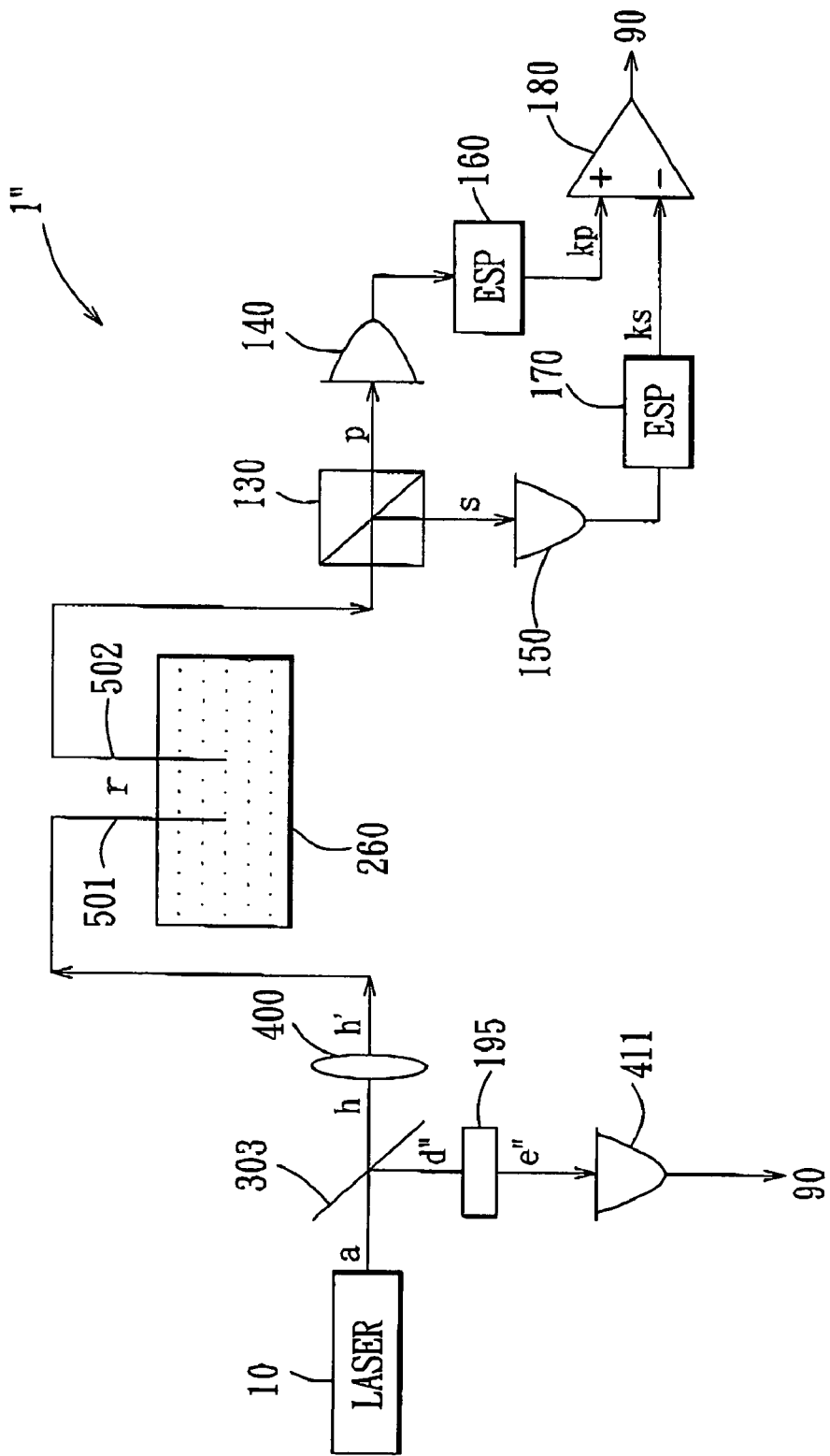
FIG. 6 is a block diagram of a spectrometer apparatus adapted for measuring an absorption coefficient and a reduced scattering coefficient of a multiple scattering medium according to the fifth preferred embodiment of the present invention.

As shown in FIG. 6, a differential amplifier 180 is used to increase the detection sensitivity and the signal-to-noise ratio (SNR) of the spectrometer apparatus 1" according to the fifth preferred embodiment of the present invention.

In this embodiment, the source light beam (a) outputted from the two-frequency laser source 10 is split into a signal beam (h) and a reference beam (d") via a beam splitter 303. The signal beam (h) is focused via a microscopic object lens 400 for optic-fiber input into an optical signal fiber 501. The optical signal fiber 501 projects the focused signal beam (h') into the scattering medium 260 to form DPPDW, which is then detected by an optical detection fiber 502 disposed at a separation distance r from the optical signal fiber 501. A polarized beam splitter 130 splits and sends a P wave component (in the X-direction) and an S wave component (in the Y-direction) of the DPPDW into respective ones of the photo detectors 140, 150 and electrical signal processors (ESPS) 160, 170 to produce P and S test heterodyne interference signals $(k_P)$, $(k_S)$, which can be expressed as in the following equations.

$$I_x(\Delta\omega t)=DC+\gamma \cos(\Delta\omega t+\Delta\Phi) \quad (14)$$

$$I_y(\Delta\omega t)=DC-\gamma \cos(\Delta\omega t+\Delta\Phi) \quad (15)$$

The differential amplifier 180 forms a balanced detector by obtaining the difference of two signal inputs and sending the resulting difference to the electrical signal processor 90. The resulting difference can be expressed as follows.

$$\Delta I=I_x-I_y=2\gamma \cos(\Delta\omega t+\Delta\Phi) \quad (16)$$

At the same time, the reference beam (d") is converted into a reference heterodyne interference signal (e") via a polarizer 195 and a photo detector 411. The reference heterodyne interference signal (e") is inputted into the electrical signal processor 90 to obtain amplitude attenuation and phase delay of the signal beam (h) with a higher SNR.

Therefore, through heterodyne interferometry and spatial coherence of the two-frequency circularly polarized photon pair, the magnitudes of the phase and amplitude of the DPPDW can be obtained from the reference and test heterodyne interference signals (e"), $(k_P)$, $(k_S)$ and the absorption coefficient $\mu_a$ and the reduced scattering coefficient $\mu_g'$ of the scattering medium 260 can be inferred from the phase delay and amplitude attenuation so as to improve the spatial resolution of images of the multiple scattering medium 260.

While the present invention has been described in connection with what is considered the most practical and preferred embodiments, it is understood that this invention is not limited to the disclosed embodiments but is intended to cover various arrangements included within the spirit and scope of the broadest interpretation and equivalent arrangements.

What is claimed is:

1. A method for measuring an absorption coefficient and a reduced scattering coefficient of a multiple scattering medium, comprising the steps of:
    outputting a source light beam using a two-frequency polarized laser, the source light beam including a mutually correlated and mutually orthogonal polarized photon pair;
    transforming the source light beam into a transformed light beam that includes a mutually parallel circularly polarized photon pair, the mutually parallel circularly polarized photon pair being one of a pair of R waves and a pair of L waves;
    splitting the transformed light beam into a signal beam and a reference beam;
    detecting and converting the reference beam into a reference heterodyne interference signal;
    focusing the signal beam and projecting the focused signal beam into the multiple scattering medium via an optical signal fiber to produce a diffused polarized photon pair density wave;
    detecting the diffused polarized photon pair density wave via an optical detection fiber that is spaced apart from the optical signal fiber;
    converting the diffused polarized photon pair density wave into a test heterodyne interference signal;
    obtaining amplitude attenuation and phase delay of the signal beam that has propagated through the multiple scattering medium based on the reference and test heterodyne interference signals; and
    inferring the absorption coefficient and the reduced scattering coefficient of the multiple scattering medium with reference to the amplitude attenuation and the phase delay thus obtained.

2. The method as claimed in claim 1, wherein the source light beam is outputted using a two-frequency circularly polarized laser, and the mutually correlated and mutually orthogonal polarized photon pair of the source light beam is circularly polarized and includes an R wave and an L wave.

3. The method as claimed in claim 1, wherein the step of transforming the source light beam includes:
    converting the mutually correlated and mutually orthogonal polarized photon pair of the source light beam into a mutually correlated and mutually orthogonal linearly polarized photon pair, which includes a P wave and an S wave, using a first $\lambda/4$ wave plate;
    converting the mutually correlated and mutually orthogonal linearly polarized photon pair into a mutually parallel linearly polarized photon pair via a polarizer; and
    converting the mutually parallel linearly polarized photon pair into the mutually parallel circularly polarized photon pair of the transformed light beam through a second $\lambda/4$ wave plate.

4. The method as claimed in claim 1, wherein:
    the source light beam is outputted using a two-frequency linearly polarized laser, and the mutually correlated and mutually orthogonal polarized photon pair of the source light beam is linearly polarized and includes a P wave and an S wave;
    the step of transforming the source light beam including
        converting the mutually correlated and mutually orthogonal polarized photon pair of the source light beam into a mutually parallel linearly polarized photon pair via a polarizer, and
        converting the mutually parallel linearly polarized photon pair into the mutually parallel circularly polarized photon pair of the transformed light beam through a λ/4 wave plate.

5. A method for measuring an absorption coefficient and a reduced scattering coefficient of a multiple scattering medium, comprising the steps of:
outputting a source light beam using a two-frequency circularly polarized laser, the source light beam including a mutually correlated and mutually orthogonal circularly polarized photon pair, the mutually correlated and mutually orthogonal circularly polarized photon pair including an R wave and an L wave;
splitting the source light beam into a signal beam and a reference beam;
converting the reference beam into a mutually parallel polarized photon pair via a polarizer;
detecting and further converting the reference beam with the mutually parallel polarized photon pair into a reference heterodyne interference signal;
focusing the signal beam and projecting the focused signal beam into the multiple scattering medium via an optical signal fiber to produce a diffused polarized photon pair density wave;
detecting the diffused polarized photon pair density wave via an optical detection fiber that is spaced apart from the optical signal fiber;
converting the detected diffused polarized photon pair density wave into a mutually parallel polarized photon pair;
further converting the mutually parallel polarized photon pair converted from the detected diffused polarized photon pair density wave into a test heterodyne interference signal;
obtaining amplitude attenuation and phase delay of the signal beam that has propagated through the multiple scattering medium based on the reference and test heterodyne interference signals; and
inferring the absorption coefficient and the reduced scattering coefficient of the multiple scattering medium with reference to the amplitude attenuation and the phase delay thus obtained.

6. A method for measuring an absorption coefficient and a reduced scattering coefficient of a multiple scattering medium, comprising the steps of:
outputting source light beams from a set of two-frequency circularly polarized lasers, the source light beams having distinct center frequencies and different beat frqeuencies, each of the source light beams including a mutually correlated and mutually orthogonal circularly polarized photon pair, the mutually correlated and mutually orthogonal circularly polarized photon pair of each of the source light beams including an R wave and an L wave;
transforming each of the source light beams into a corresponding transformed light beam that includes a mutually parallel circularly polarized photon pair, the mutually parallel circularly polarized photon pair of each of the transformed light beams being one of a pair of R waves and a pair of L waves;
splitting the transformed light beams into a signal beam and a reference beam;
detecting and converting the reference beam into a set of filtered reference heterodyne interference signals;
focusing the signal beam and projecting the focused signal beam into the multiple scattering medium via an optical signal fiber to produce a diffused polarized photon pair density wave;
detecting the diffused polarized photon pair density wave via an optical detection fiber that is spaced apart from the optical signal fiber;
converting the diffused polarized photon pair density wave into a set of filtered test heterodyne interference signals;
obtaining amplitude attenuation and phase delay of the signal beam that has propagated through the multiple scattering medium based on the filtered reference and test heterodyne interference signals; and
inferring the absorption coefficient and the reduced scattering coefficient of the multiple scattering medium with reference to the amplitude attenuation and the phase delay thus obtained.

7. The method as claimed in claim 6, wherein detection and conversion of the reference beam is conducted using a set of photo detectors and a set of band-pass filters coupled respectively to the photo detectors, the band-pass filters having distinct pass-band frequency ranges.

8. A spectrometer apparatus adapted for measuring an absorption coefficient and a reduced scattering coefficient of a multiple scattering medium, said spectrometer apparatus comprising:
a set of two-frequency circularly polarized lasers for outputting a set of source light beams, the source light beams having distinct center frequencies and different beat frequencies, each of the source light beams including a mutually correlated and mutually orthogonal circularly polarized photon pair, the mutually correlated and mutually orthogonal circularly polarized photon pair of each of the source light beams including an R wave and an L wave;
a set of beam-transforming units, each including a first λ/4 wave plate, a polarizer, and a second λ/4 wave plate arranged in sequence at an output side of a respective one of said lasers, each of said beam-transforming units transforming a respective one of the source light beams into a transformed light beam that includes a mutually parallel circularly polarized photon pair, the mutually parallel circularly polarized photon pair of each of the transformed light beams being one of a pair of R waves and a pair of L waves;
a beam splitter for splitting the transformed light beams from said beam-transforming units into a signal beam and a reference beam;
a set of first photo detectors for detecting the reference beam from said beam splitter, and a set of reference band-pass filters coupled respectively to said first photo detectors, said reference band-pass filters having distinct pass-band frequency ranges, and converting the reference beam detected by said first photo detectors into a set of filtered reference heterodyne interference signals;
an object lens for focusing the signal beam from said beam splitter;
an optical signal fiber adapted for projecting the focused signal beam from said object lens into the multiple scattering medium to produce a diffused polarized photon pair density wave;
an optical detection fiber spaced apart from said optical signal fiber and adapted for detecting the diffused polarized photon pair density wave;
a set of second photo detectors for receiving the diffused polarized photon pair density wave detected by said second photo detectors, and a set of test band-pass filters coupled respectively to said second photo detectors, said test band-pass filters having distinct pass-band frequency ranges, and converting the diffused polarized photon pair density wave processed by said second photo detectors into a set of filtered test heterodyne interference signals;

a set of signal processors, each of which is coupled to a respective one of said reference band-pass filters and a respective one of said test band-pass filters, each of said signal processors obtaining amplitude attenuation and phase delay of the signal beam that has propagated through the multiple scattering medium based on the filtered reference and test heterodyne interference signals received thereby, and inferring the absorption coefficient and the reduced scattering coefficient of the multiple scattering medium with reference to the amplitude attenuation and the phase delay obtained thereby.

* * * * *